US00PP37052P2

(12) United States Plant Patent
Huber

(10) Patent No.: US PP37,052 P2
(45) Date of Patent: Oct. 21, 2025

(54) ***DAHLIA* PLANT NAMED 'LeeAnn's BA67C'**

(50) Latin Name: *Dahlia hybrida*
Varietal Denomination: LeeAnn's BA67C

(71) Applicant: LeeAnn Huber, Greencastle, PA (US)

(72) Inventor: LeeAnn Huber, Greencastle, PA (US)

(73) Assignee: Coseytown Flowers llc, State Line, PA (US)

( * ) Notice: Subject to any disclaimer, the term of this patent is extended or adjusted under 35 U.S.C. 154(b) by 0 days.

(21) Appl. No.: 19/028,225

(22) Filed: Jan. 17, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321

CPC . A01H 5/02; A01H 5/00; A01H 6/144; A01H 6/14

See application file for complete search history.

(56) References Cited

PUBLICATIONS

Dahlia Barn retrieved on Apr. 1, 2025 at https://www.dahliabarn.com/product/caitlins-joy/, 2 pp. (Year: 2025).*

* cited by examiner

*Primary Examiner* — June Hwu
(74) *Attorney, Agent, or Firm* — Cassandra Bright

(57) ABSTRACT

A new and distinct cultivar of *Dahlia* plant named 'LeeAnn's BA67C' is disclosed, characterized by bright pink, fully double full ball form blooms on plants with a strong, upright growth habit. Flowers are held above the foliage canopy and have a consistent quality throughout the growing season. Flowering stems have an above average strength with a firm blossom attachment. Inflorescences have strong postproduction quality. The new variety is a *Dahlia* typically produced for cut flower purposes, or garden or landscape.

2 Drawing Sheets

Figure 1:
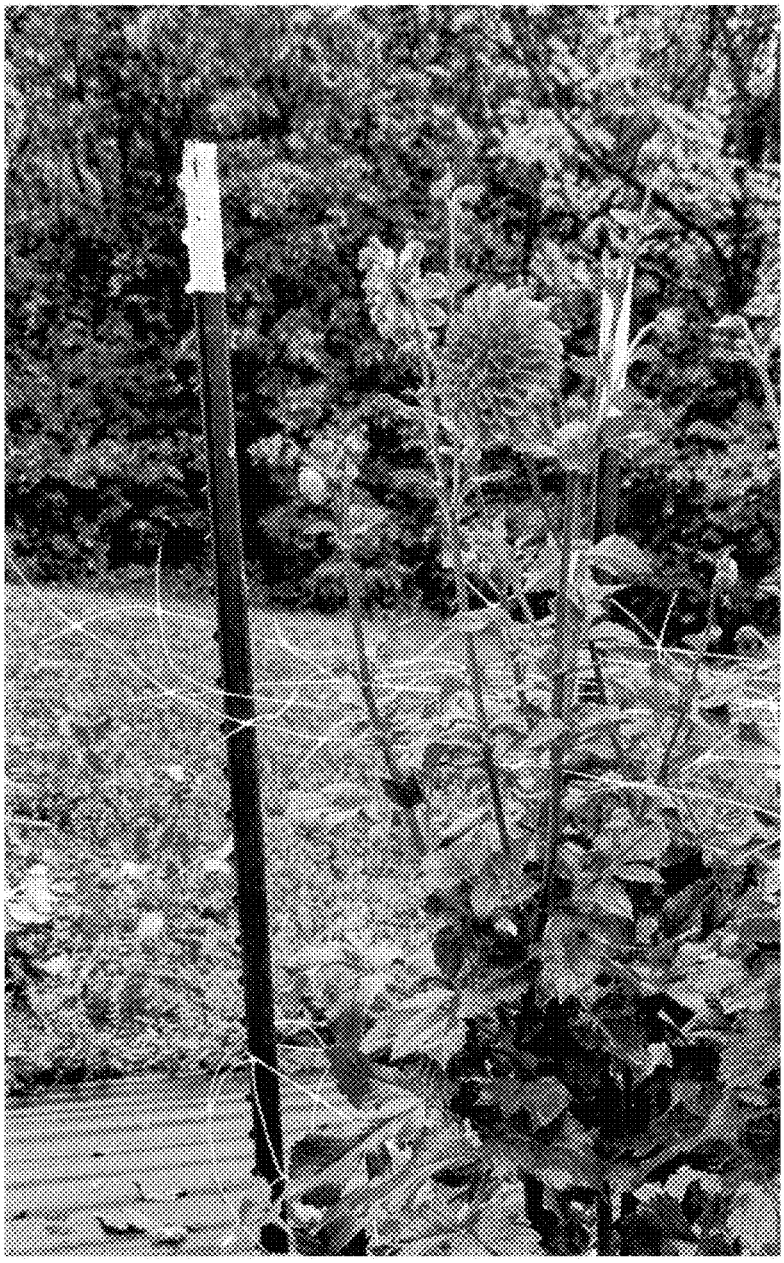

Latin name of the genus and species: *Dahlia hybrida.*
Variety denomination: 'LeeAnn's BA67C'.

BACKGROUND OF THE INVENTION

The new *Dahlia* cultivar is a product of a planned breeding program conducted by the inventor, in Greencastle, Pennsylvania. The objective of the breeding program was to produce new *Dahlia* varieties with improved performance in open field conditions and produce cut flowers suitable for transport and sale. The open-pollination resulting in this new variety was made during the Fall of 2020.

The seed parent is the unpatented, variety of *Dahlia* 'Coralie'. The pollen parent is unidentified. 'LeeAnn's BA67C' was intentionally selected in the Summer of 2021 based on the criteria of strong, upright growth, as well as free branching and flowers held above the leaf canopy. The new cultivar was selected in Greencastle, Pennsylvania.

Asexual reproduction of the new cultivar was first performed by root divisions by the inventor in Greencastle, Pennsylvania in the Spring of 2022 and has shown that the unique features of this cultivar are stable and reproduced true to type in successive generations.

SUMMARY OF THE INVENTION

The new cultivar 'LeeAnn's BA67C' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's BA67C'. These characteristics in combination distinguish 'LeeAnn's BA67C' as a new and distinct *Dahlia* cultivar:

1. Strong, upright growth habit requiring minimal to no field support.
2. Free branching.
3. Consistency of bloom quality throughout the growing season.
4. Flower held above the leaf canopy.
5. Strong flowering stems.
6. Firm blossom attachment.
7. Bright pink, full, ball type inflorescence.
8. Strong postproduction inflorescence quality.

PARENT COMPARISON

Plants of the new cultivar 'LeeAnn's BA67C' are similar to plants of the seed parent, in some horticultural characteristics, however, plants of the new cultivar 'LeeAnn's BA67C' differ in the following;

1 'Coralie' is lighter in color with similar color pigmentation on both the upper and lower ray floret surfaces.
2. 'Coralie' inflorescence bloom size is larger than 'LeeAnn's BA67C'.
3. Bloom form of 'Coralie' form is considered to be formal decorative; the new cultivar as a fully double ball form bloom.
4. Ray floret color of 'Coralie' will shift from pink to yellow as temperatures and daylight hours shift in the season. Bloom color of the new cultivar is more stable.

5. 'LeeAnn's BA67C' has longer post production vase life than 'Coralie'.

The pollen parent cannot be identified with certainty.

COMMERCIAL COMPARISON

Plants of the new cultivar 'LeeAnn's BA67C' are comparable to the variety *Dahlia* 'Caitlin's Joy', unpatented. The two *Dahlia* varieties are similar in most horticultural characteristics; however, the new variety 'LeeAnn's BA67C' differs in the following:

1. 'LeeAnn's BA67C' has more purple color to the entire inflorescence than 'Caitlin's Joy'. Ray florets of 'LeeAnn's BA67C' open Red-Purple 72A with light streaks of 72C. Ray florets of 'Caitlin's Joy' open Red-Purple 58B and 58C with a tinge of Red 40D, making a more coral appearance overall.
2. 'Caitlin's Joy' is a shorter plant by approximately 20%.
3. 'Caitlin's Joy' has [a] smaller leaves in both length and width by about 20 to 30%.
4. 'Caitlin's Joy' has shorter lateral branch internode lengths by about 30%.

BRIEF DESCRIPTION OF THE PHOTOGRAPHS

The accompanying photograph in FIG. 1 illustrates in full color a typical flowering plant of 'LeeAnn's BA67C' grown outdoors, in the ground under cut flower production conditions. Age of the plant photographed is approximately 130 days from a rooted cutting.

Figure 2:
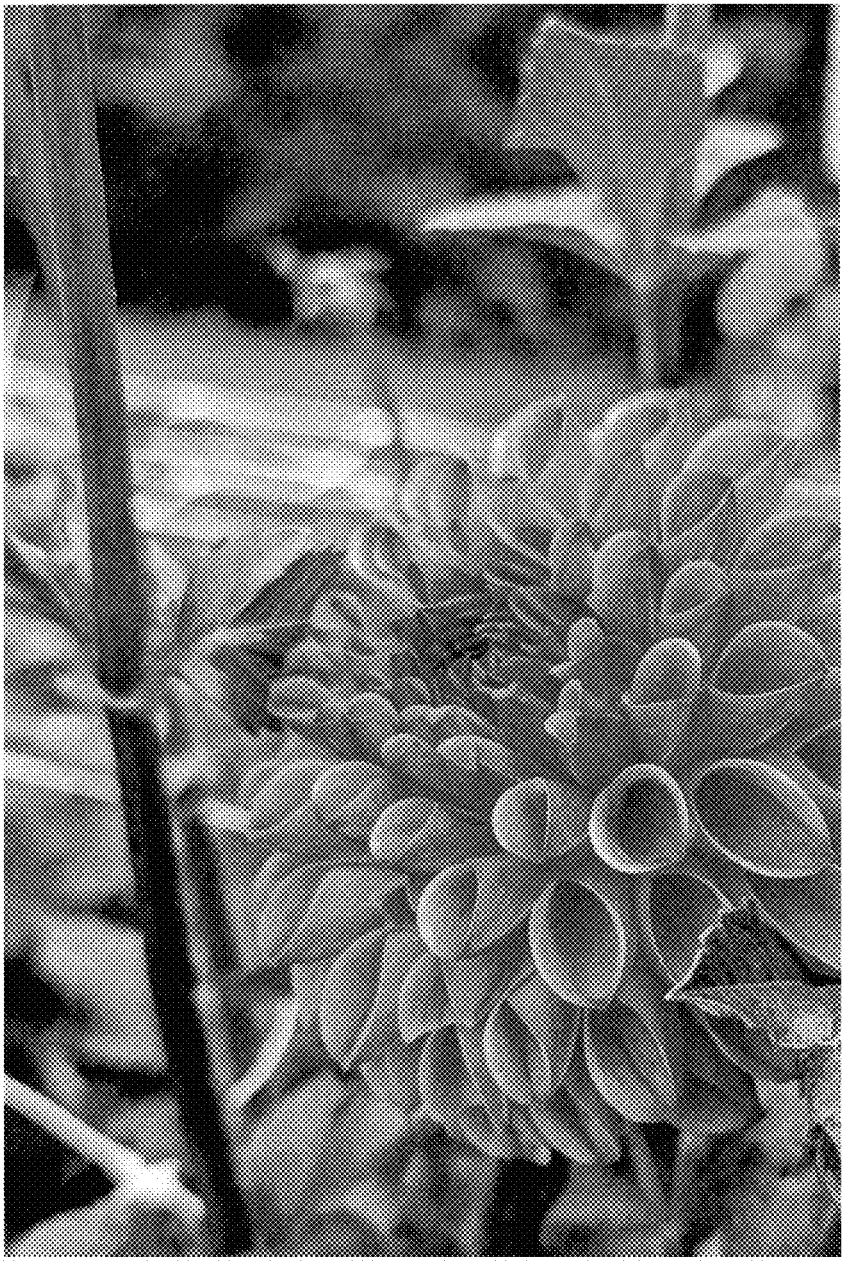

FIG. 2 illustrates a close-up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society R.H.S. Colour Chart 2015 except where general terms of ordinary dictionary significance are used. The following observations and measurements describe 'LeeAnn's BA67C' plants grown outdoors, in production cut flower rows in Greencastle, PA. The average growing season for outdoor cut flower production runs from May through mid-October or 24 weeks. The terminal bud is pinched off the *Dahlia* around 4-6 weeks of age. Temperatures ranged from about 23° C. to 39° C. during the day 7° C. to 23° C. at night. General light conditions are bright, normal sunlight. Botanical data was collected between May and September. Measurements and numerical values represent averages of typical plant types.

Botanical classification: *Dahlia hybrida* 'LeeAnn's BA67C'.

PROPAGATION

Time to initiate roots: (March) Winter: 5 to 18 days at approximately 18° C.

Root description: Freely branching, fine rootlets with canescent hairs.

PLANT

Plant type: Herbaceous flowering perennial.

*Plant height.*—57.3 inches.

*Plant spread.*—19.3 inches.

*Lateral branch length.*—31.9 inches.

*Lateral branch diameter base.*—12.8 mm.

*Lateral branch diameter apex.*—11.8 mm.

$2^{nd}$ *internode length.*—163.9 mm.

*Angle of bloom stem from lateral branch average.*—16.4 deg.

*Branch strength.*—Exceptional.

*Branch texture.*—Semi-glossy, smooth.

*Branch color.*—Near RHS Yellow-Green 146B tinted with Greyed-Purple 187A.

FOLIAGE

Leaf:

*Arrangement.*—Leaves opposite; leaves may be single, or compound with three or five leaflets.

*Shape.*—Ovate.

*Apex.*—Acuminate.

*Base.*—Attenuate.

*Margin.*—Serrated.

*Length.*—Single leaves: about 104.6 mm. Compound leaves with three leaflets: Average 123.3 mm. Compound leaves with five leaflets: average 167.4 mm.

*Width.*—Single leaves: average 69.4 mm. Compound leaves with three leaflets: average 132.7 mm. Compound leaves with five leaflets: average 201.7 mm.

*Venation pattern.*—Pinnate.

*Texture.*—Upper surface: Smooth. Lower surface: Smooth.

*Leaf color.*—Developing foliage: Upper Surface Yellow-Green 147A. Lower Surface Yellow-Green 147B. Fully developed: Upper Surface 147A. Lower Surface 147B.

Rachis (3 and 5 leaf leaflets):

*Length.*—6 to 8 cm.

*Diameter.*—5 mm.

*Color.*—Upper surface: Yellow-Green 146B. Lower Surface: Yellow-Green 146B.

*Texture.*—Glabrous all surfaces.

*Leaf wing.*—Absent.

*Petiole length.*—Single leaves: About 22.4 mm. Compound leaves with three leaflets: about 53.6 mm. Compound leaves with five leaflets: about 54.8 mm.

*Petiole diameter.*—Single leaves: about 2.8 mm. Compound leaves with three leaflets: about 3.6 mm. Compound leaves with five leaflets: about 5.1 mm.

*Petiole texture.*—Upper and lower surfaces: smooth and glabrous.

*Petiole color.*—Upper Surface: Overall hue Greyed-Orange 176B with a base color of 146A. Lower surface: Green 143D.

Stipule: Not present.

FLOWER

Days to flowering from rooted cutting: Plants begin to bloom around 80 days after planting; continuously blooming until the season ending frost in Pennsylvania while maintaining good ray floret count and inflorescence form.

Inflorescence and flower type and habit: Fully double ball form *Dahlia* with ray and disc florets positioned above the foliage on very strong peduncles with an upright to 45° blossom position.

Rate of flower opening: 16 to 18 days from bud to fully opened flower.

Flower longevity on plant: Inflorescence maintains good substance (attractive color with good moisture content) on the plant for about 18 days.

Flower longevity as a cut flower: For about 6-7 days as a cut flower (fresh water at room temperature).

Persistent or self-cleaning: Self Cleaning.

Inflorescence:

*Bloom position*.—Positioned above the foliage on the strong peduncles (stalk) with upright to slightly outwardly face.

*Flower scent*.—Not fragrant.

*Inflorescence bud*.—Shape: Oblate. Texture: Glabrous. Appearance: Semi-glossy. Color: Yellow-Green 145A. Height: 12.3 mm. Diameter: 20.1 mm.

*Inflorescence size*.—Diameter: About 75 mm. Height or Depth: About 75 mm. Receptacle diameter: About 4 mm. Disc Diameter: About 5 mm.

*Ray florets*.—Length: About 33.3 mm. Width: About 24.3 mm. Density: Dense. Shape: Obovate. Apex: Obtuse. Base: Aequilateral. Aspect: Initially upright to roughly perpendicular to the peduncle to reflexed, cupped. Profile in cross section at mid-point: Strongly concave with margins overlapping. Texture: Upper surface-Smooth, keeled, 2 keels, velvety with gold diamond dust, velvety. Lower surface-Smooth, glabrous, white diamond dust, velvety. Number of ray florets per inflorescence: About 204 arranged in 15 whorls. Color: Fully opened: Inner Surface: Red-Purple 67C, lightly streaked 71D. Base Yellow 3A. Outer Surface: Red-Purple 67C, lightly streaked 71B. Base Yellow 3A. When opening: Inner Surface: Red-Purple 72A, very lightly streaked 72C. Base Yellow 2A. Outer Surface: Red-Purple 72A, very lightly. streaked 72C. Base Yellow 2A.

*Disc florets*.—Shape: Tubular. Apex: Acute. Length: About 10.1 mm. Diameter, base: About 1 mm. Number of disc florets per inflorescence: Average 84. Immature color: Apex Yellow-Orange 15A, mid section 23A, base 6B.

*Phyllaries*.—Quantity per inflorescence: Average 8. Length: About 16.5 mm. Width: About 6.6 mm. Arrangement: Whorl. Shape: Ovate. Apex: Obtuse. Base: Truncate. Margin: Entire. Texture: Upper surface: Smooth, glabrous, waxy. Lower surface: Waxy with sulcate grooves. Color: Upper Surface 137C, Lower Surface 137B.

*Peduncles*.—Strength of stem: Exceptional. Aspect: very strong, mostly upright. Angle of bloom from lateral branch 12-24 degrees. Texture: smooth with sulcate grooves. Color: Lower surface Yellow-Green 146B, upper surface Greyed-Orange 177A. Length: 75.4 cm. Diameter at base: 7.5 mm. Diameter at Apex: 3.2 mm.

REPRODUCTIVE ORGANS

Stamen: Quantity per disc floret: 5.

*Stamen attachment*.—Filament adnate to ventral surface of corolla.

*Stamen length*.—about 10.7 mm.

*Stamen color*.—Yellow-Green 150D.

*Anther shape*.—Linear.

*Anther length*.—About 4.8 mm.

*Anther color*.—23A.

*Pollen amount*.—Present.

*Pistil quantity per disc floret*.—1.

*Pistil length*.—About 19.3 mm.

*Stigma shape*.—Bifurcate.

*Stigma form*.—Plumose.

*Stigma length*.—About 4.0 mm.

*Stigma width*.—About 0.6 mm.

*Stigma color*.—21A.

*Ovary position*.—Inferior.

*Ovary shape*.—Truncate.

*Ovary color*.—2C.

*Ovary length*.—About 2.6 mm.

*Ovary width*.—About 1.1 mm.

Ray florets: No reproductive structures present.

OTHER CHARACTERISTICS

Fruit/seed:

*Seed length*.—10.3 mm.

*Seed width*.—3.5 mm.

*Seed color*.—Brown 200A.

Disease/pest resistance: Neither resistance nor susceptibility to normal diseases and pests of *Dahlia* has been observed.

Weather and climate performance: Plants of the new *Dahlia* have excellent tolerance to heat and high UV index, resisting wilting and fading in field grown conditions. Daylight length has minimal effects on bud and bloom production, maintaining cut flower output into late season light and weather conditions.

Temperature range: Grown in any zone as an annual. Can be overwintered in Zone 6 and 7 with protective mulch. Can be perennialized in zones 8 and above.

What is claimed is:

1. A new and distinct cultivar of *Dahlia* plant named 'LeeAnn's BA67C' as herein illustrated and described.

* * * * *